United States Patent [19]

Anderson, Jr.

[11] Patent Number: 4,586,733

[45] Date of Patent: May 6, 1986

[54] ADAPTER COUPLING FOR LIQUID CHROMATOGRAPHY DEVICE

[75] Inventor: James M. Anderson, Jr., Arlington Heights, Ill.

[73] Assignee: Alltech Associates, Inc., Deerfield, Ill.

[21] Appl. No.: 581,372

[22] Filed: Feb. 17, 1984

[51] Int. Cl.[4] .......................... F16L 25/00; F16L 33/00
[52] U.S. Cl. ...................................... 285/12; 285/239; 285/330; 285/386
[58] Field of Search ................. 285/12, 330, 354, 386, 285/423, 256, 259, 238

[56] References Cited

U.S. PATENT DOCUMENTS

| | | | |
|---|---|---|---|
| 3,248,138 | 4/1966 | Bradbury | 285/238 |
| 3,408,099 | 10/1968 | Appleton | 285/259 |
| 3,512,807 | 5/1970 | Moran | 285/330 |
| 4,313,828 | 2/1982 | Brownlee | 285/109 |
| 4,529,230 | 7/1985 | Fatula | 285/DIG. 12 |

FOREIGN PATENT DOCUMENTS

| | | | |
|---|---|---|---|
| 0533384 | 11/1956 | Canada | 285/354 |
| 0558775 | 6/1958 | Canada | 285/354 |
| 2729359 | 1/1978 | Fed. Rep. of Germany | 285/177 |
| 1456143 | 11/1976 | United Kingdom | 285/423 |

Primary Examiner—Richard J. Scanlan, Jr.
Assistant Examiner—Anthony Knight
Attorney, Agent, or Firm—Lee, Smith & Zickert

[57] ABSTRACT

A universal adapter coupling for liquid chromatography equipment, such as columns. The adapter coupling comprises two threaded segments which are matingly secured to one another and has an elongated sealing insert located in a central passage which extends axially between opposite ends of the holder. The insert protrudes from one of the ends of the holder and has a collar which is captured within a cavity in the holder. Ferrule seats are provided at opposite ends of the insert so that the adapter coupling can be used either as a female or a male coupling.

9 Claims, 3 Drawing Figures

ADAPTER COUPLING FOR LIQUID CHROMATOGRAPHY DEVICE

BACKGROUND OF THE INVENTION

This invention pertains to liquid chromatography equipment, and in particular to a universal adapter coupling which is used to adapt a liquid chromatography device, such as a column, so that the column can be connected to other liquid chromatography equipment without tools and while accommodating a variety of different fittings which normally are not interchangeable.

Liquid chromatography equipment is fabricated by a number of different manufacturers. Many of the manufacturers have adopted unique dimensions for couplings for their equipment which are not compatible with couplings of other manufacturers. As a result, the equipment of different manufacturers is either not interchangeable or can be made interchangeable only with the use of connecting tubing and low volume unions. Doing so, however, adds dead volume to the chromatography equipment and requires the use of bulky, space-consuming fittings. In addition, the mode of adapting between two types of equipment provided thereby is usually incompatible with the equipment of many other manufacturers of liquid chromatography equipment, requiring substitution of different adapters if the equipment of yet different manufacturers is to be interconnected.

The primary use of the invention is for universally adapting liquid chromatography columns so that they are compatible with a variety of fitting types of various manufacturers. Alltech Associates, Inc., Deerfield, Ill., the assignee of the present invention, has in the past, sold a universal adapter kit which can be connected to a column to adapt the column to fit the chromatography equipment of manufacturers other than that of the column. However, the kit requires an individual ferrule and a particular male or female connecting fitting depending on the type of column being adapted. Thus, while the kit is "universal", different parts must be used to adapt various columns. No single part is uniquely available to itself adapt any of a number of different columns having incompatible fittings.

SUMMARY OF THE INVENTION

The invention provides a unique universal adapter coupling for liquid chromatography equipment which, as an assembled unit, adapts the equipment of many manufacturers without further modification. The universal adapter coupling comprises a holder including axially aligned first and second holder segments which are matingly secured to one another. A central passage extends axially between opposite ends of the holder through the holder segments when they are secured together. A central cavity is formed in the holder in registration with the central passage. An elongated sealing insert is located in the holder, the insert being situated in the passage and having an enlarged collar which is located in the cavity. The insert has an integral ferrule seat at one end and includes a longitudinal bore extending the length thereof to permit fluid flow.

In the preferred embodiment of the invention, one of the holder elements has a male thread and the other of the holder elements has a corresponding female thread so that the holder elements may be threadedly secured to one another. Due to the geometry of the adapter coupling, in the preferred embodiment of the invention one of the holder segments is shaped to contain the cavity and that holder segment also has the male threads which fit within the female threads of the other holder segment.

The insert has a portion extending through the passage and outwardly beyond one of the ends of the holder. A ferrule seat is located on the end of the extending portion and the extending portion has a male thread between the end of the holder and the ferrule seat for connection of the adapter coupling to a liquid chromatography device. In the preferred embodiment of the invention, a second integral ferrule seat is located at the other end of the insert within the central passage which includes female threads so that the adapter coupling may be connected to a male-threaded liquid chromatography device.

The central cavity closely fits about and accommodates the collar of the insert. In order to prevent rotation of the insert within the holder, the collar has a flattened side and a corresponding dimple is formed in the holder element having the female thread in a location to engage the flattened side.

The insert is preferrably manufactured from an inert plastic material, such as a polyimide, while the holder is manufactured from metal, such as stainless steel. The adapter coupling therefore can be engaged with liquid chromatography equipment without tools and by tightening with finger tightening pressure. In order to facilitate gripping of the exterior of the holder, knurling is provided on the holder segments.

BRIEF DESCRIPTION OF THE DRAWINGS

The invention is described in greater detail in the following description of an example embodying the best mode of the invention, taken in conjunction with the drawings, in which.

DESCRIPTION OF EXAMPLE EMBODYING BEST MODE OF THE INVENTION

Figure 3:
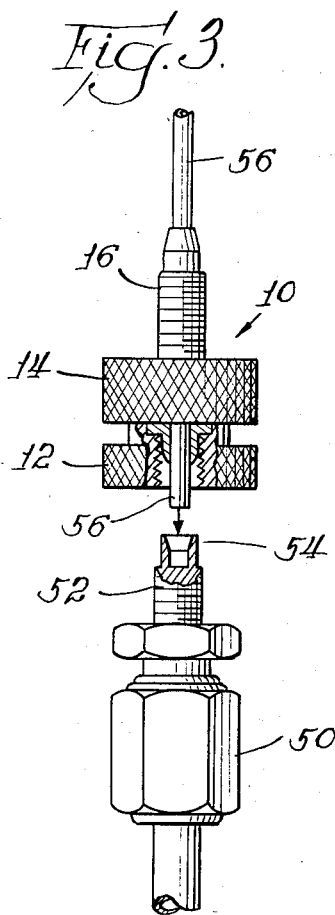
FIG. 3 is a view similar to FIG. 2 but showing the adapter coupling of the invention engaging an item of liquid chromatography equipment provided with a male coupling end.
Figure 2:
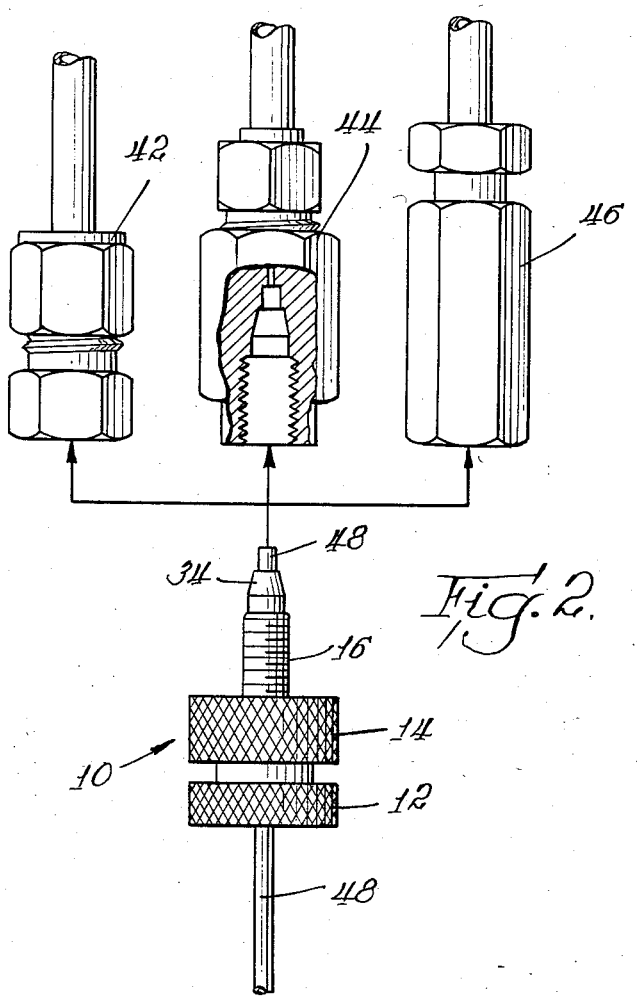
FIG. 2 illustrates connection of the invention to any one of three different examples of liquid chromatography equipment provided with a female end.
Figure 1:
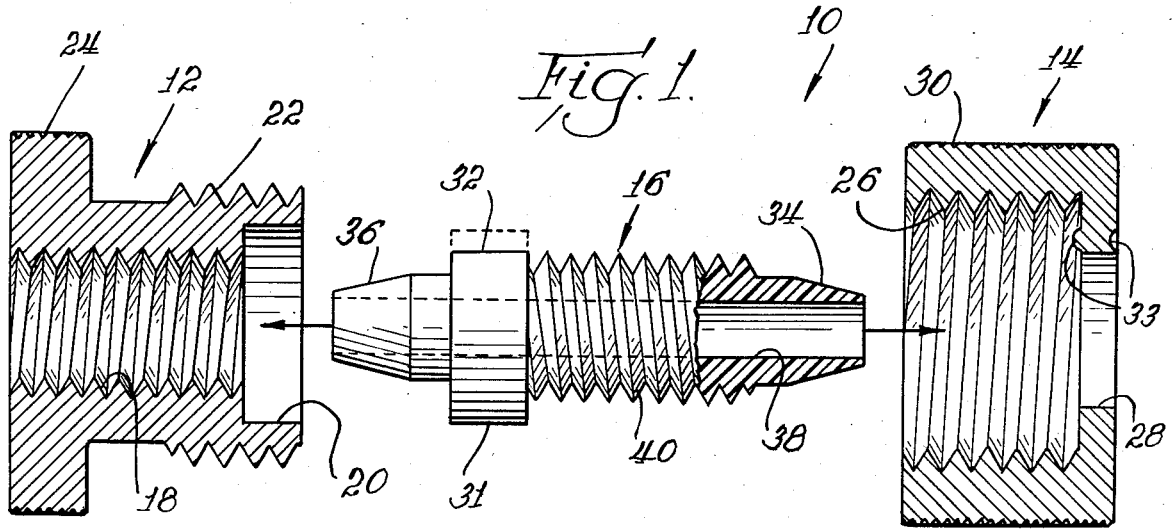
FIG. 1 is an exploded, generally cross-sectional view of the invention showing the means of interengagement of the three parts thereof.

An adapter coupling according to the invention is shown generally at 10 in the drawings and, as shown in FIG. 1, comprises, as primary components, first and second holder segments 12 and 14, and an elongated sealing insert 16. The holder segments 12 and 14, when engaged with one another with the sealing insert 16 contained therein, form the assembled adapter coupling 10, as best shown in FIGS. 2 and 3.

The first holder segment 12 includes an internally threaded passage 18 extending axially therethrough and a central cavity 20 in registration with the passage 18 which, as described below, accommodates a collar of the sealing insert 16. The holder segment 12 has an external, male connecting thread 22 and, for purposes of gripping by the user, has an expanded flange or collar 24 having knurling or the like thereon to enhance the user's grip.

The second holder segment 14 has a central passage therethrough which includes a female connecting thread 26 corresponding to and shaped to engage the male thread 22 of the first holder segment 12. A further passage portion 28 completes the passage through the second holder segment 14. As can be seen from the drawings, when the holder segments 12 and 14 are engaged, the passage 18, cavity 20, and passage portion 28 form a central passage extending axially between opposite ends of the assembled holder formed by the holder segments 12 and 14. In a fashion similar to that of the first holder segment 12, the second holder segment 14 includes knurling 30 on the exterior thereof to improve the grip of the user.

The insert 16 has an enlarged collar 31 which is shaped to fit within the cavity 20. The depth of the collar 31 is at least as great as the depth of the cavity 20 so that when the holder segments 12 and 14 are engaged, the collar 31 is snuggly and securely held in the cavity 20 between the holder segments 12 and 14. In addition, the collar 31 is provided with a flattened side 32. A corresponding dimple 33 is formed in the holder segment 14 to engage the flattened side 32 when the holder 10 is assembled. The dimple 33, in combination with the void in the collar 31 formed by the flattened side 32, thus prevents rotation of the insert 16.

The insert 16 also has integral ferrule seats 34 and 36 at opposite ends thereof. A longitudinal bore 38 extends the length of the insert 16 and, as shown in FIG. 1, the insert includes threads 40 extending between the collar 31 and the ferrule seat 34.

When the adapter coupling 10 is assembled as shown in FIGS. 2 and 3, the threaded portion of the insert 16 extends outwardly beyond the holder segment 14, thus providing a male attachment portion of the adapter coupling 10. At the same time, due to the placement of the ferrule seat 36 immediately adjacent the collar 31, and due to the length of the threaded passage 18, the ferrule seat 36 is located within the threaded passage 18, thus providing a female attachment portion of the adapter coupling 10. The adapter coupling 10 thus may be used universally to couple to liquid chromatography equipment provided with either male or female connecting ends.

FIG. 2 illustrates use of the adapter coupling 10 to connect to three different liquid chromatography columns 42, 44 and 46. A length of tubing 48 extends through the adapter coupling 10 through the bore 38 and may extend to any desired distance beyond the adapter coupling 10 and into the associated column 42, 44 or 46, as desired. When engaged with one of the columns 42, 44 or 46, the ferrule seat 34 is compressed about the tubing 48 to seal the interface between the tubing 48 and the ferrule seat 34. At the same time, the exterior of the ferrule seat 34 seals to the coupled column 42, 44 or 46. Thus, a complete and effective seal is provided by the adapter coupling 10 between the tubing 48 and the connected column 42, 44 or 46. Since the insert 16 is made of a somewhat flexible material, the ferrule seat 34 will thus seat within the column of any one of a number of manufacturers and engage and adjust to a corresponding seat of a number of different sizes or shapes. See FIGS. 2 and 3 for illustrations of such column seats.

In FIG. 3, the adapter coupling 10 is used to adapt a column 50 having a male-threaded end 52. The adapter 10 is threaded onto the male-threaded end 52 of the column 50. When the ferrule end 54 of the column 50 engages the ferrule seat 36, a complete and effective seal is provided between the column 50 and a length of tubing 56 in the same fashion as the coupling described in connection with FIG. 2.

The length of the passage 18 and the length of the threaded portion of the insert 16 extending beyond the holder segment 14 are sufficient so that the adapter coupling 10 may be engaged with the liquid chromatography equipment of many different manufacturers. It is evident that the various dimensions shown in the drawings can be altered depending on the requirements demanded of the adapter coupling 10. Various changes can be made to the invention without departing from the spirit thereof or scope of the following claims.

What is claimed is:

1. A universal adapter for holding a piece of tubing in fluid sealing relationship alternatively with either an internally or externally threaded coupling member for liquid chromatography equipment, said adapter comprising
   a. a holder including axially aligned first and second holder segments,
   b. means matingly securing together said first and second holder segments,
   c. a central passage extending axially between opposite ends of said holder through said holder segments when secured to one another, at least a portion of the central passage extending through said first holder segment being internally threaded for mating with a coupling member having external threads,
   d. an enlarged central cavity in said holder in registration with said central passage, and
   e. an elogated sealing insert for said holder, said insert being situated partially in said passage and including
      i. a first end portion disposed wholly within the internally threaded portion of the central passage of said first holder segment,
      ii. a second end portion extending outwardly beyond said second holder segment, said second portion being externally threaded for mating with a coupling member having internal threads,
      iii. a longitudinal bore extending the length of said insert and adapted to receive therethrough a piece of tubing,
      iv. an integral ferrule seat formed at each end portion thereof, and
      v. an enlarged collar intermediate said first and second end portions, said collar being located in the enlarged central cavity of said holder,
   whereby said first and second holder segments will hold said insert in position for sealing engagement with the coupling member when the adapter and coupling member are threadedly engaged.

2. A universal adapter according to claim 1 in which said securing means comprises a female thread in one of said holder segments and a corresponding male thread in the other of said holder segments.

3. A universal adapter according to claim 1 in which said internal thread extends between the outer end of said first holder segment and said central cavity.

4. A universal adapter according to claim 1 including means to prevent rotation of said insert.

5. A universal adapter according to claim 4 in which said means to prevent rotation comprises a flattened side of said collar and corresponding a dimple in one of said holder segments in registration with said flattened side when said coupling is assembled.

6. A universal adapter according to claim 1 including means on the exterior of said holder to facilitate gripping thereof.

7. A universal adapter according to claim 1 including means on the exterior of said holder to facilitate gripping thereof.

8. The universal adapter of claim 1 wherein said holder central cavity is defined at each end by said first and second holder segment respectively and said insert collar is gripped between said holder segments to prevent axial movement of said insert.

9. The universal adapter of claim 1 wherein said insert collar is disposed adjacent the ferrule seat formed on said first end portion.

* * * * *